(12) United States Patent
Kim (10) Patent No.: US 9,463,270 B2
(45) Date of Patent: Oct. 11, 2016

(54) INGREDIENT SEPARATOR

(71) Applicant: DONGKOO BIO & PHARMA CO., LTD., Seoul (KR)

(72) Inventor: Jun-Woo Kim, Daegu (KR)

(73) Assignee: DONGKOO BIO & PHARMA CO., LTD., Seoul (KR)

( * ) Notice: Subject to any disclaimer, the term of this patent is extended or adjusted under 35 U.S.C. 154(b) by 204 days.

(21) Appl. No.: 14/241,002

(22) PCT Filed: Jan. 18, 2013

(86) PCT No.: PCT/KR2013/000390
§ 371 (c)(1),
(2) Date: Feb. 25, 2014

(87) PCT Pub. No.: WO2013/133529
PCT Pub. Date: Sep. 12, 2013

(65) Prior Publication Data
US 2014/0231335 A1  Aug. 21, 2014

(30) Foreign Application Priority Data

Mar. 5, 2012 (KR) .......................... 10-2012-0022304

(51) Int. Cl.
*A61M 1/02* (2006.01)
*A61M 1/36* (2006.01)
(Continued)

(52) U.S. Cl.
CPC ........... *A61M 1/3693* (2013.01); *A61M 1/029* (2013.01); *B01L 3/5021* (2013.01); *B01L 3/5635* (2013.01);
(Continued)

(58) Field of Classification Search
CPC .... A61M 1/028; A61M 1/3693; A61M 1/34; A61M 1/3472; A61M 2202/0427; A61M 2202/0437; A61M 2039/1077; A61M 2039/1083; A61M 2039/1088; B01L 3/5021; B01L 3/5635; B01L 3/561; B01L 2300/0681; B01L 2300/0851; B01L 2300/042; B01L 2300/046; B01L 2400/0478; B01L 2200/026; C12M 47/04; B04B 1/06; B04B 1/08; B04B 5/02
See application file for complete search history.

(56) References Cited

U.S. PATENT DOCUMENTS

| 3,765,537 A * | 10/1973 | Rosenberg ............ A61M 5/165 210/446 |
| 2006/0278588 A1* | 12/2006 | Woodell-May ......... B01L 3/502 210/787 |
| 2013/0011311 A1* | 1/2013 | Kim ....................... A61B 5/153 422/548 |

FOREIGN PATENT DOCUMENTS

| JP | 2007-304016 A | 11/2007 |
| JP | 2008-104789 A | 5/2008 |

(Continued)

OTHER PUBLICATIONS

International Search Report for corresponding International Application No. PCT/KR2013/000390 mailed on Apr. 29, 2013.

*Primary Examiner* — Lucas Stelling
(74) *Attorney, Agent, or Firm* — Billion & Armitage; Benjamin Armitage (57) ABSTRACT

Disclosed is a blood ingredient separator capable of assuring purity of such as separated blood components or stem cells as well as preventing contamination by ambient air during the process of separating components, while simplifying the processes compared to the related art. The ingredient separator includes: a hollow body which includes a flow tube formed at one end portion thereof for communicating body fluids, and a stopper disposed at the other end portion thereof; and a plunger which is movably installed back and forth in the body to vary a space between the flow tube and a top of the plunger thereof; wherein the plunger has a collection portion formed on the top thereof, and a backward movement of the plunger is limited by the stopper.

8 Claims, 10 Drawing Sheets

(51) Int. Cl.
  *B01L 3/00* (2006.01)
  *C12M 1/00* (2006.01)
(52) U.S. Cl.
  CPC .............. *A61M 2202/0427* (2013.01); *A61M 2202/0437* (2013.01); *B01L 2200/026* (2013.01); *B01L 2300/0681* (2013.01); *B01L 2300/0851* (2013.01); *B01L 2400/0478* (2013.01); *C12M 47/04* (2013.01)

(56) References Cited

FOREIGN PATENT DOCUMENTS

| | | | |
|---|---|---|---|
| KR | 10-0917795 | B1 | 9/2009 |
| KR | 10-0988220 | B1 | 10/2010 |
| KR | 10-0988221 | B1 | 10/2010 |
| KR | WO 2011118907 | A2 * | 9/2011 ............. A61B 5/153 |

* cited by examiner

INGREDIENT SEPARATOR

RELATED APPLICATIONS

This application is a National Stage Application of PCT/KR2013/000390, filed on 18 Jan. 2013, which claims the benefit of Korean Application No. 10-2012-0022304, filed on 5 Mar. 2012, and which applications are incorporated herein by reference. A claim of priority to all, to the extent appropriate, is made.

BACKGROUND

Blood is divided largely into blood cells and plasma. The blood cells consist of red blood cells, white blood cells and platelets, and the plasma consists mainly of water including blood coagulating factors, electrolyte, etc. which are indispensable for maintaining life.

Blood components are separated for various medical purposes. For this, various processes for extracting component elements by separating blood are widely used. Among them, a process of centrifugally separating blood by using specific gravity differences of blood components by a centrifuge and a process of extracting component elements by using specific compositions are widely used.

The centrifugal separation process refers to a process of separating layer by layer each of the blood components that compose blood by using specific gravity differences generated by a centrifugal force of the centrifuge rotating at a specific velocity. If blood is centrifugally separated, the heaviest red blood cells are placed at the bottom layer, and white blood cells and platelets are placed above the red blood cell layer. Finally a plasma layer or serum layer is placed at upper portion.

In this case, the platelet rich plasma called PRP is located relatively below the plasma and contains many growth factors such as cytokine, PDGF, TGF-BETA and VEGF. It is clarified in data such as theses and dissertations that PRP shows good effects in healing skin diseases and wounds in particular.

In addition, plasma with few platelets known as PPP (platelet poor plasma) is used in auto blood filler applications or auto plasma derived cosmetics. The auto blood filler is used in medical operations in which it is changed into a PPP gel form through adding temperature treatment and then injected into the skin.

SUMMARY

The present disclosure relates to an ingredient separator, and more specifically to an ingredient separator capable of assuring purity of such as separated blood components or stem cells as well as preventing contamination by ambient air during the process of separating components, while simplifying the processes compared to the related art.

According to another example of the disclosure, an ingredient separator comprises a hollow body which includes a flow tube formed at one end portion thereof for flowing body fluids, and a stopper disposed at the other end portion thereof; and a plunger which is movably installed back and forth in the body to vary a space between the flow tube and a top of the plunger thereof; wherein the plunger has a collection portion formed on the top thereof, and a backward movement of the plunger is limited by the stopper.

The details of one or more examples are set forth in the accompanying drawings and the description below. Other features, objects, and advantages will be apparent from the description and drawings, and from the claims.

DETAILED DESCRIPTION

Blood components are separated for various medical purposes. For this, various processes for extracting component elements by separating blood are widely used. It has been true that such specific operations need more convenient and advanced methods for extracting specific components from blood. Therefore, in order to separate such blood components, the present applicant has presented a method and an apparatus for separating blood components.

However, in some related art (Korean Patent Registration Nos. 10-0988220 and 10-0988221), a pressing screw and push rod are configured separately, so not only is there a disadvantage in storage thereof but also it is inconvenient to work therewith because the pressing screw and push rod should be used selectively.

Further, in the related art, there have been no inventions ever presented including the above patents or any simple kits to carry out the separating method for stem cells. In particular, in the case of adipose-derived stem cells, the quantity extracted in comparison with the volume of the whole stock solution (a mixed liquid of fat and collagenase solution) is very small, so it is difficult to obtain a high-purity stem cell by using such inventions of the above patents.

In consideration of the above-mentioned circumstances, it is an object of the present disclosure to provide an ingredient separator capable of both assuring purity of such as separated blood components or stem cells and preventing contamination by ambient air during the process of separating components, while simplifying the processes compared to the related art.

In order to accomplish the foregoing objects, according to an aspect of the present disclosure, there is provided an ingredient separator including: a hollow body which includes a flow tube formed at one end portion thereof for flowing body fluids, and a stopper disposed at the other end portion thereof; and a plunger which is movably installed back and forth in the body to vary a space between the flow tube and a top of the plunger thereof; wherein the plunger has a collection portion formed on the top thereof, and a backward movement of the plunger is limited by the stopper.

The "body fluid" mentioned in the present disclosure has a concept of including both a liquid material such as blood, lymph fluid, bone marrow extracts, umbilical cord blood, or the like which are directly obtained from a body, and substances in which materials obtained from the body are solved or mixed in other solvents such as a mixture of fats and collagenase solution.

Herein, the stopper is a female screw unit which is coupled to the other end of the body. The pressing unit includes both a pressing screw body to screw with the female screw unit and a push tube having a plurality of (multiple) tube holes formed on an outer periphery. A plurality of pressing protrusions on the pressing screw body are able to be inserted into the portions of the tube holes in a radial direction, and a pressing unit further is inserted to the body.

In addition, the stopper has a fixing protrusion which is detachably inserted in a fixing hole formed in the other end portion of the body. The stopper is capable of stopping the body fluids by contacting to the lower portion thereof so as to inject a constant amount of the body fluids into the body when the injection of the body fluids is completed, and preventing the plunger from being separated downward during injection or centrifugal processing of the body fluids.

Further, the stopper has a lower plug fitted therein to close the other end of the body.

Further, the pressing screw body is an elastic tube which is inserted in the push tube and has a slit cutaway in a lengthwise direction thereof, and the pressing screw body has a plurality of pressing protrusions formed on the outer periphery thereof so as to be selectively inserted in the tube holes and screwed with a female thread formed in the female screw unit.

Further, the plunger has a coupling protrusion formed on a lower portion thereof facing the other end portion of the body through a neck portion, and the pressing screw body includes a latch portion fixed on one end portion thereof to engage with the neck portion when the pressing protrusions are hidden in the push tube.

Further, a connector is fitted to the flow tube to connect an ingredient collector therewith.

Further, the connector has at least one cell strainer installed therein.

Further, the connector has one connector fitting portion formed on one side thereof and two connector fitting portions formed on the other side thereof.

Furthermore, when two or more cell strainers are installed inside the connector, each of the cell strainers has a different size of meshes with respect to each other.

According to the present disclosure, it is possible to reduce the time and costs required in the separation work of the blood components. In particular, by separating by applying pressure upward in the order of PPP and PRP that have light specific gravity, the mixing of the blood cells is minimized or prevented, and the degree of purity of separated PRP and PPP is high.

In addition, since blood components are moved in a state isolated from ambient air by a connector between the ingredient separator and the ingredient collector, it is possible to prevent contamination by ambient air. Therefore, it is possible to prevent infection of pathogens or complications that may occur due to air contamination of the blood during the blood separation process.

Further, according to the present disclosure, it is also possible to separate stem cells. By employing a plunger, with a unique shape capable of collecting stem cells, in order to separate the minimum volume thereof compared to the stock solution, high-purity stem cells can be easily extracted. Therefore, it is possible to reduce treatment costs dramatically when the treatments using stem cells are performed.

Hereinafter, embodiments of the present disclosure will be described in detail with reference to the accompanying drawings. Referring to the drawings, wherein like reference characters designate like or corresponding parts throughout the several views. In the embodiments of the present disclosure, a detailed description of publicly known functions and configurations that are judged to be able to make the purport of the present disclosure unnecessarily obscure are omitted.

Figure 1:
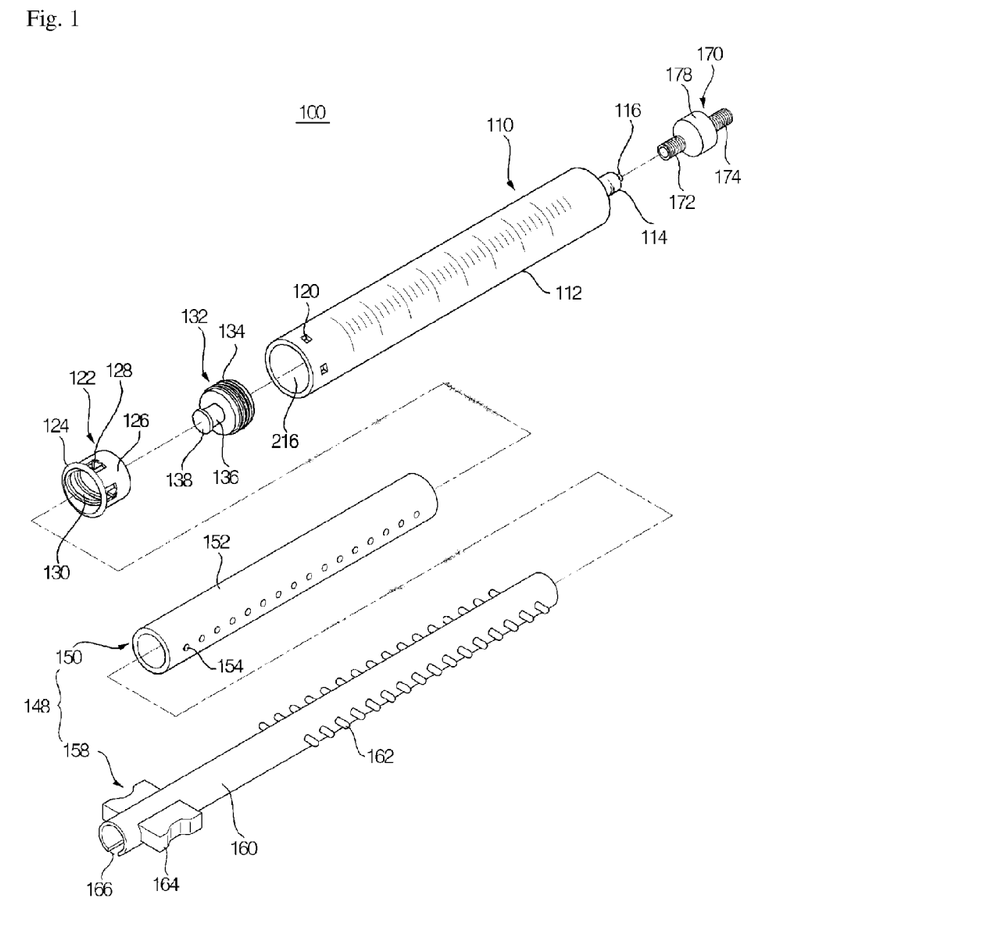
FIG. 1 is an exploded perspective view of an ingredient separator according to an embodiment of the present disclosure.

An ingredient separator 100 according to an embodiment of the present disclosure can include a hollow body 110, a plunger 132 which is movably installed in the body 110.

The body 110 includes a flow tube 116 formed at one end portion thereof. The body fluid is injected into the body 110 or extracted from the body 110 through the flow tube 116. A female screw unit 122 plays a role as a stopper which is coupled to the other end portion of the body 110 thereof.

The body 110 can be made of a transparent material so as to allow the inside thereof to be seen, and it may be made of plastic, glass or the like. The flow tube 116 is provided with a tube fitting portion 114 to which the connector 170 or the upper plug 180 is screwed. For this, the tube fitting portion 114 may have a female or male thread formed on an inner or outer surface thereof, and the embodiment of the present disclosure employs a female thread formed on the inner surface thereof. A connector 170 or an upper plug 180 may be selectively coupled to the tube fitting portion 114.

The body 110 has fixing holes 120 which are formed on the other end portion thereof for detachably fixing the female screw unit 122. In addition, a female screw body 126 of the female screw unit 122 has fixing protrusions 128 which are detachably inserted in the fixing holes 120. The female screw unit 122 has a female thread 130 formed on an inner surface thereof. In addition, the female screw body 126 has a stop flange 124 to define an insert range of the female screw unit 122 during inserting into the other end portion of the body 110. Further, an upper end portion of the female screw unit 122 plays a role of a stopper capable of stopping the body fluids by contacting to the lower portion of the plunger 132 so as to inject a constant amount thereof into the body 110 when the injection of the body fluids is completed, and preventing the plunger from being separated outward during injection or centrifugal processing of the body fluids.

It is also possible for the female screw unit 122 to be formed integrally on the other end portion of the body 110, however, as mentioned above, it can be favorable that these are separately formed in two parts in terms of productivity of forming molds.

Figure 7:
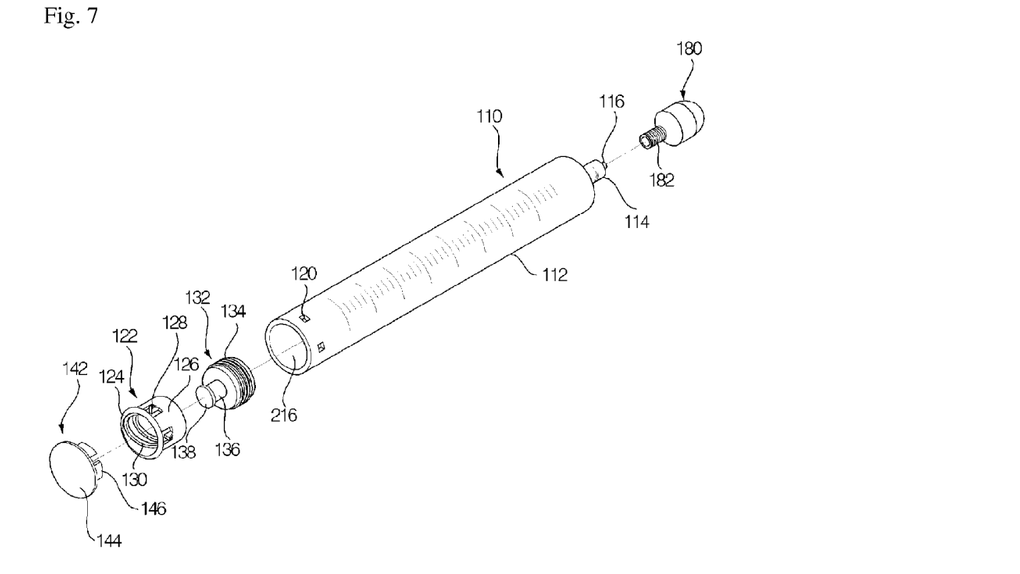
FIG. 7 is an exploded perspective view illustrating the shape that an upper plug and a lower plug are coupled to the ingredient separator of FIG. 1.

In addition, a lower plug 142 is fitted in the other end of the female screw unit 122. The lower plug 142 can prevent foreign matters from flowing into the body 110. When injecting the body fluids into the ingredient separator 100 with the lower plug 142 fitted thereto, since air contained in the body 110 is discharged through openings formed by the fixing holes 120 and the fixing protrusions 128, it is difficult to discharge the air compared to the case without the lower plug 142. That is, it is possible to silently inject the body fluids into the ingredient separator 100 due to an increased resistance by the decreased openings for the discharge of the air.

The lower plug 142 is provide with a plug body 144 having a larger outer diameter than that of the lower end of the body 110 or the female screw unit 122 so as to cover the lower end of the body 110 or the female screw unit 122. The plug body 144 has plug legs 146 formed on one side thereof so as to fix the lower plug 142 to the lower end of the body 110 or the female screw unit 122 by radial enlargement in a fitted state therein. Alternatively, the lower plug 142 may have a male thread formed on the annular surface thereof so as to screw with a thread formed in the female screw unit 122 (not shown), instead of the plug legs 146.

When the plunger 132 is moved back and forth in the body 110, a space between the flow tube 116 and the plunger 132 can be varied. Accordingly, it is possible to introduce or discharge a fluid such as a body fluid between the flow tube 116 and the plunger 132.

The plunger 132 includes sealing members 134 mounted on the periphery thereof so as to seal the above mentioned space. Accordingly, it is possible to prevent a substance contained in the space from being leaked toward the other end portion of the body 110. In addition, a collection portion is formed on the top of the plunger 132 so as to easily collect a specific substance. The collection portion may be a concave groove 140 or a substantially conical groove with a low center portion which is formed on the top of the plunger 132.

Accordingly, due to the unique geometrical characteristics of the collection portion, it is possible to reliably collect very small amount of specific substances which have high specific gravities.

The plunger 132 has a coupling protrusion 138 which is formed on the lower portion. A coupling protrusion 138 connects with the plunger 132 through a neck portion 136. The coupling protrusion 138 engages with a pressing unit 148 to be described below.

Figure 2:
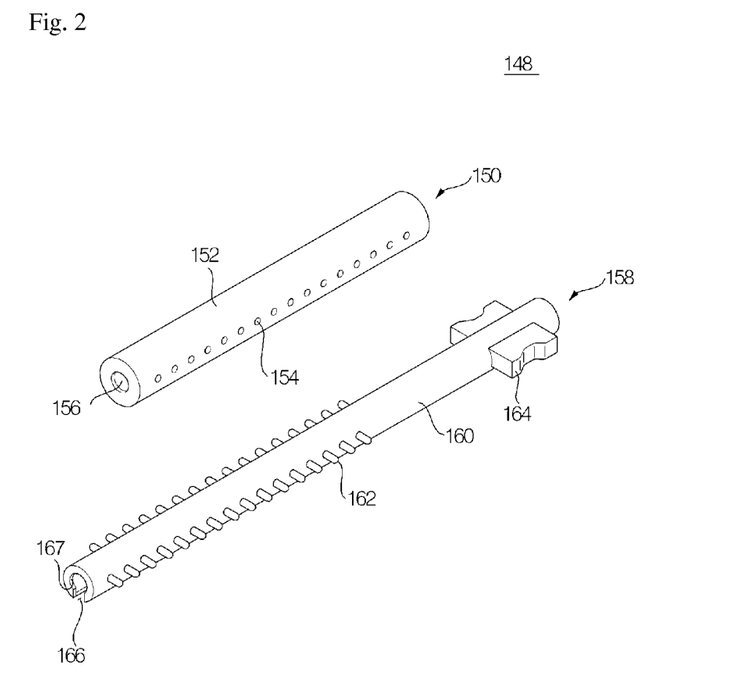
FIG. 2 is an exploded perspective view of a pressing unit used in the ingredient separator of FIG. 1.

The pressing unit 148 includes a pressing screw body 158 and a push tube 150. The pressing screw body 158 screws with the female screw unit 122, and the push tube 150 has multiple tube holes 154 formed on an outer periphery thereof. Multiple pressing protrusions 162 of the pressing screw body 158 are selectively inserted into tube holes 122 in a radial direction.

The outer diameter of a push tube body 152 is smaller than the inner diameter of the female thread 130. In addition, the push tube 150 has a penetration hole 156 formed at one end portion (in a direction facing the plunger 132). Therefore, the coupling protrusion 138 of the plunger 132 can penetrate a penetration hole 156. In an assembled state, the upper end of the push tube 150 contacts to the bottom of the plunger 132, thereby it is possible to push up the plunger 132.

The pressing screw body 158 is an elastic tube 160 having a slit 166 which is a cutaway in a lengthwise direction thereof. Therefore, if an external force is applied to the pressing screw body, opposite faces defining the slit contact each other to form a substantially circular shaped cross section, while if the external force is removed therefrom, opposite faces defining the slit are separated from each other due to an elastic force stored therein. In addition, the pressing screw body 158 has multiple pressing protrusions 162 which are formed on the outer periphery. Therefore, the pressing protrusions can be inserted into the tube holes 154 and can be screwed with a female thread formed in the female screw unit 122. Further, a grip 164 may be formed on the end portion of the pressing screw body 158 for easy griping.

Figure 3:
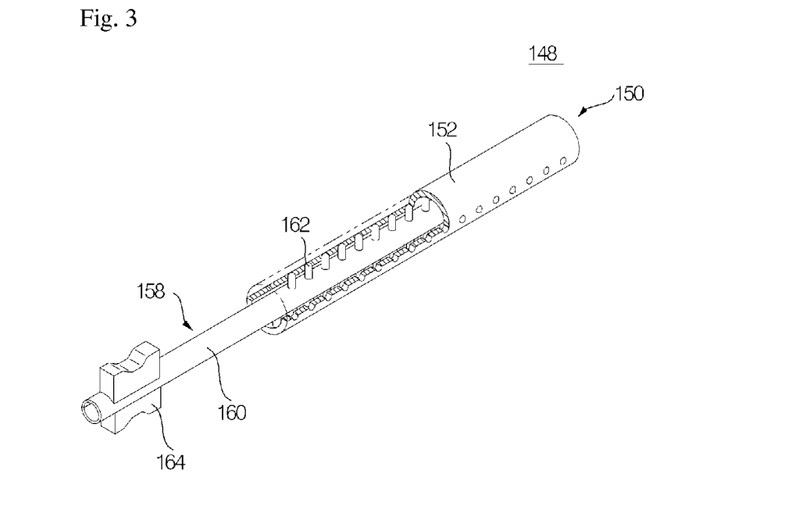
FIG. 3 is a partially cutaway perspective view illustrating the state that pressing protrusions of a pressing screw body are hidden inside a push tube body in the pressing unit of FIG. 2.
Figure 5:
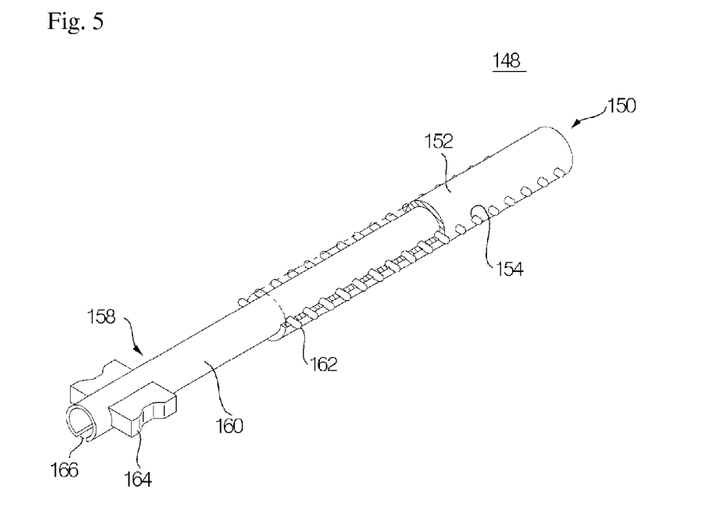
FIG. 5 is a partially cutaway perspective view illustrating the state that pressing protrusions of the pressing screw body are protruded outside of the push tube body in the pressing unit of FIG. 2.

Accordingly, if the pressing screw body 158 inside the push tube 150 is rotated, the pressing protrusions 162 are hidden in the push tube 150 as shown in FIG. 3. Conversely, if the pressing protrusions 162 are inserted into the tube holes 154, the pressing protrusions 162 can be protruded toward the outside of the push tube 150 through the tube holes 154 as shown in FIG. 5.

Figure 4:
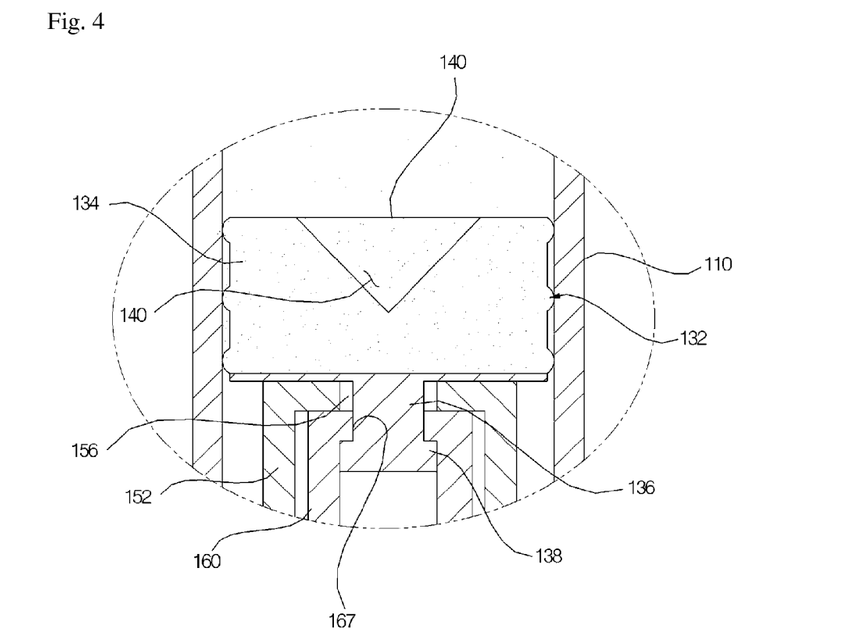
FIG. 4 is an enlarged cross-sectional view illustrating the shape that a coupling protrusion of a plunger is latched to a latch portion of the pressing screw body in the state of FIG. 3.
Figure 6:
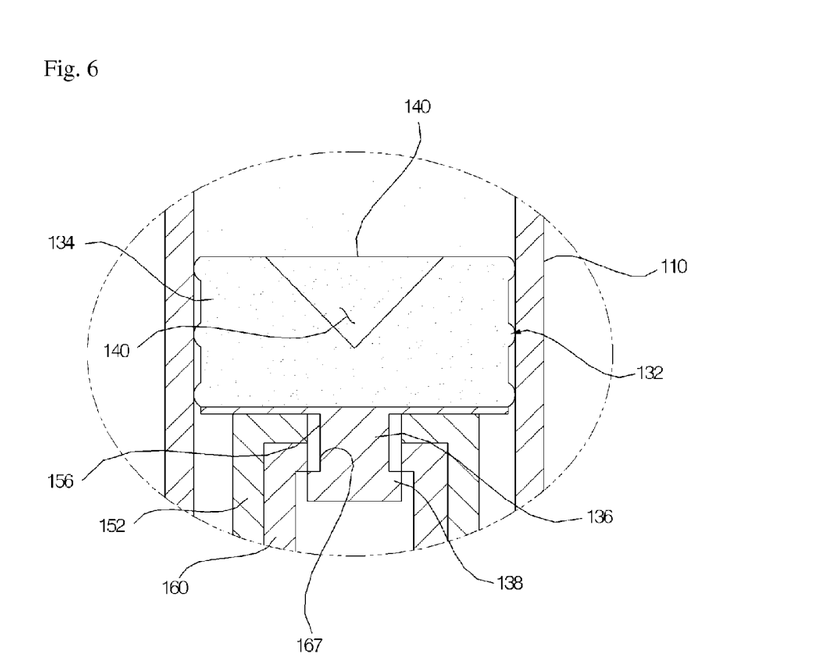
FIG. 6 is an enlarged cross-sectional view illustrating the shape that the coupling protrusion of the plunger is unlatched with the latch portion of the pressing screw body in the state of FIG. 5.

In addition, a latch portion 167 is formed at the top of the pressing screw body 158. So the latch portion 167 can latch with the coupling protrusion 138. The latch portion 167 is formed at the top of the pressing screw body 158 in a bent shape. Therefore, when the pressing screw body 158 is in a non-contracted state wherein the opposite faces defining the slit are separated from each other, the coupling protrusion 138 can pass through the latch portion 167. Conversely, when the pressing screw body 158 is in a contracted state wherein the opposite faces defining the slit contact each other, the latch portion 167 grasps the neck portion 136. As a result, the pressing unit 148 and the plunger 132 can be moved together.

The ingredient separator 100 according to the present disclosure can have the above mentioned configuration. Hereinafter, a process for separating the body fluids using the ingredient separator 100 will be described.

First, a process for separating the blood into the PPP and PRP will be described.

At first, blood is collected using a separate syringe, and the collected blood is introduced in the ingredient separator 100. In this time, the ingredient separator 100 should be maintained in a state that the plunger 132 is in contact with the one end portion thereof. In this regard, the syringe may be connected with the ingredient separator 100 using the connector 170 shown in FIG. 9. In particular, if the lower plug 142 is fitted to the ingredient separator 100, air remaining in the ingredient separator 100 can be slowly discharged outside and the body fluids can be silently introduced therein. Thereby, in some embodiments it is preferable that the ingredient separator 100 is maintained with the lower plug 142 fitted thereto.

Then, the upper side of the ingredient separator 100 is closed by the upper plug 180. The upper plug 180 has an upper plug thread 182 to screw with the thread formed in tube fitting portion 114. The flow tube 116 is inserted in a space formed in a center of the upper plug thread 182.

Figure 8:
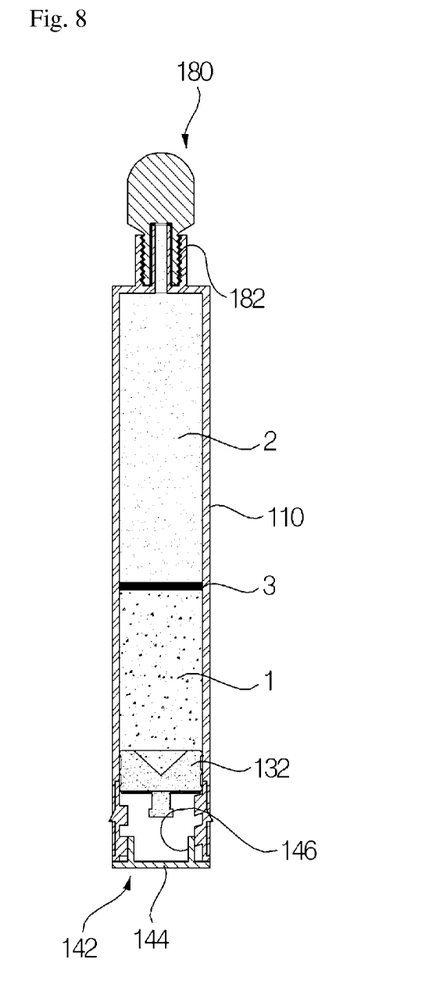
FIG. 8 is a cross-sectional view illustrating the state that blood is introduced in the ingredient separator with the plugs fitted thereto in FIG. 7 to separate the blood layer by layer using a centrifuge.

Next, the blood components in the ingredient separator 100 are separated layer by layer through a centrifugation process as shown in FIG. 8. When mounting the ingredient separator 100 in a centrifuge, the ingredient separator 100 is installed in a way that the upper plug 180 is positioned on the upper side and the lower plug 142 is positioned on the lower side. As a result, PPP 2 is placed in an upper layer in the body 110, red blood cells 1 are placed in a lower layer, and PRP 3 is placed between PPP 2 and the red blood cells 1.

Figure 9:
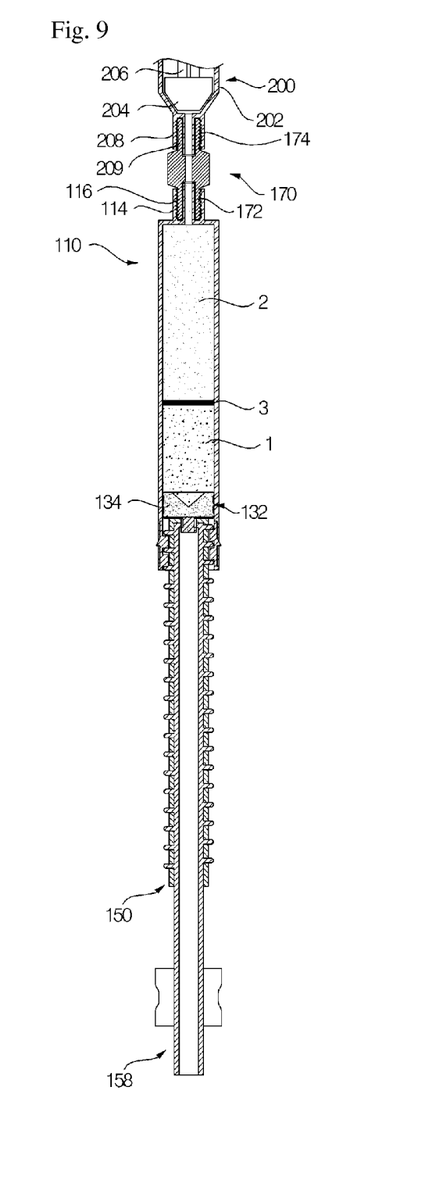
FIG. 9 is a cross-sectional view illustrating the state that an ingredient collector is connected to the ingredient separator with the upper plug removed therefrom through a connector, and the pressing unit is coupled in the ingredient separator with the lower plug removed therefrom of FIG. 8.

Then, after the upper plug 180 is separated from the body, one end of the connector 170 is connected to the tube fitting portion 114, and then a separate ingredient collector 200 is connected to the other end of the connector 170.

As shown in FIG. 9, the connector 170 has connector fitting portions 172 and 174 bilaterally. The connector 170 can be screwed with the thread of tube fitting portion 114. Herein, the inside of connector 170 and the tube fitting portion are communicated with each other through a hole formed in the connector fitting portions 172 and 174. In particular, the connector 170 may be provided with a cell strainer (not shown) installed in an internal space thereof in order to filter unnecessary substances or foreign materials. The cell strainer may include a mesh (net) structure having a size of each mesh of 100 μm or less. The reason why the mesh with a size of 100 μm or less can be preferable is that the materials or cells with a size of 100 μm or less can pass the smallest capillary easily. As a result, there may be no risks to form clogging in a human body.

The ingredient collector 200 may employ a general syringe. The ingredient collector 200 includes a container 202 having a space formed therein, a piston 204 which is movably installed in the container 202, a push rod 206 whose one end is connected to the piston 204, and a connecting tube 208 which is formed at one end of the container 202.

In addition, the pressing unit 148 is inserted in the body 110 after the lower plug 142 is separated from the ingredient separator 100. The pressing unit 148 may be inserted in a state that the pressing protrusions 162 of the pressing screw body 158 are not initially protruded and then protruded through the tube holes after completion of insertion. Otherwise, the pressing unit 148 may be inserted in a state that the pressing protrusions 162 are initially protruded through the tube holes and then the pressing protrusions 162 are screwed with the thread of female screw unit 122 to approach to the plunger 132. In this regard, the former way can reduce the work time.

Conversely, if the later way may be used, it is possible to move the intended components upward silently without making the components mixed inside the body 110.

Figure 10:
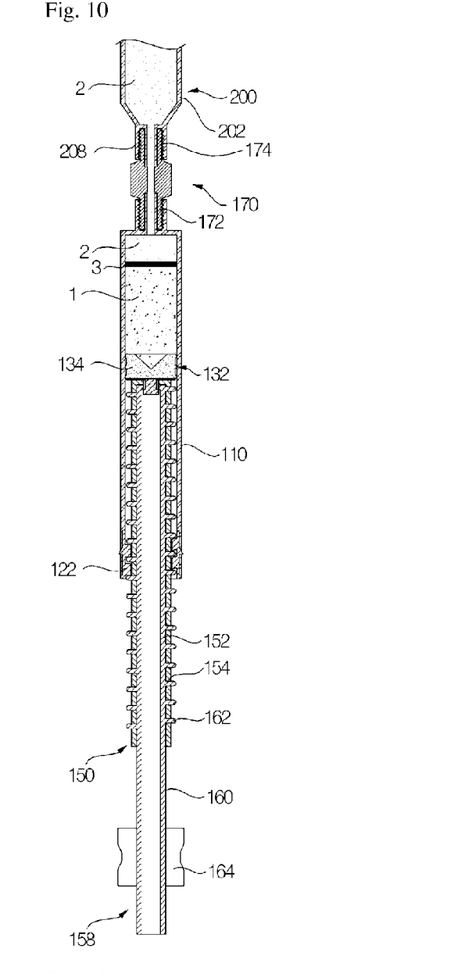
FIG. 10 is a cross-sectional view illustrating the state that blood components placed in an upper side of the ingredient separator are pushed up by pressing upward the pressing screw body from the state of FIG. 9 to supply the blood components into the ingredient collector connected to the ingredient separator through the connector.
Figure 11:
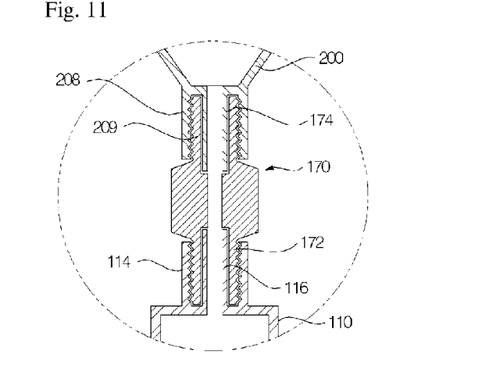
FIG. 11 is an enlarged cross-sectional view illustrating the connector for connecting the ingredient collector and the ingredient separator of FIG. 9.

When the pressing unit 148 approaches to the bottom of the plunger 132 by rotating the pressing unit 148 (in this state, the pressing protrusions 162 are protruded outside), the coupling protrusion 138 passes both the penetration hole 156 of the push tube 150 and the latch portion 167 of the pressing screw body 158 without engagement therebetween. Therefore, if the pressing unit 148 continuously rotates, the pressing unit 148 presses the plunger 132 upward, and PPP 2 is firstly moved upward and discharged into the ingredient collector 200 through the connector 170. After the PPP 2 is completely discharged, a new ingredient collector is connected to the connector 170. If the pressing unit 148 again rotates, the PRP 1 is moved through the connector 170, and thereby it is possible to obtain the PRP 1. After the PRP is introduced in the ingredient collector, the ingredient collector is connected to one end of the connector having the cell strainer, and a new ingredient collector is connected to the other end of the connector. Thereby, it is possible to further perform a process of meshing (cell straining) the collected components through the mesh. The reason for meshing the components is that filtering foreign materials or clumped cells is important in order to prevent thrombosis. Therefore, it is possible to separate the intended blood components by the above processes.

In addition, if there is a need to retreat the plunger 132, the elastic tube is rotated using the grip 164 with the push tube 150 contacted to the bottom of the plunger 132, then the pressing protrusions 162 are hidden in the push tube 150. At this time, the neck portion 136 of the plunger 132 is gripped by the latch portion 167 of the pressing screw body 158 as shown in FIG. 4, and thereby the pressing unit 148 and the plunger 132 can be moved in a body. At this time, if the pressing unit 148 is pulled, the plunger 132 is retreated in the body.

Next, a method of separating stem cells will be described. First, in order to extract adipose-derived stem cells, fats are obtained from a human body using a technique such as liposuction.

For this, a decanting or centrifugation process is firstly performed on the extracted fats to remove water and obtain pure fats.

Next, a collagenase solution mixed with physiological saline and collagenase is added to the obtained pure fats, and the mixture is again decanted or centrifuged to obtain a solution containing stem cells collected on a lower side. Then, the obtained stem cell containing solution is introduced in the ingredient separator 100.

Figure 12:
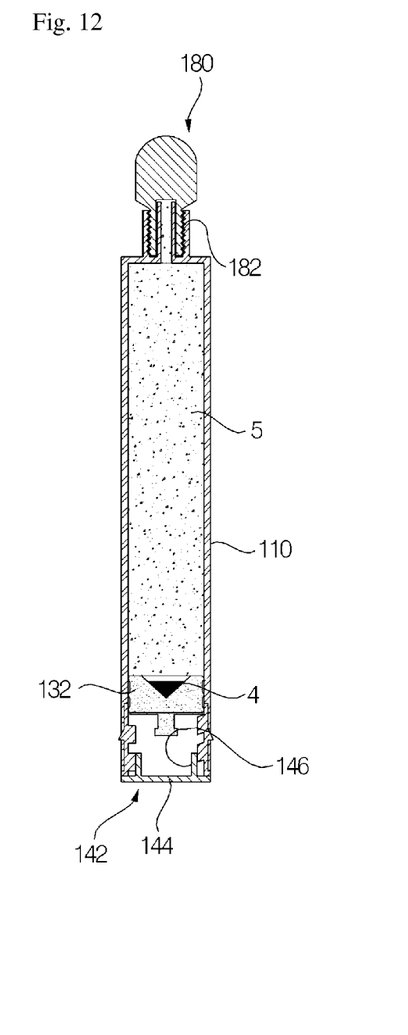
FIG. 12 is a cross-sectional view illustrating the state that solutions containing stem cells obtained from fats are introduced in the ingredient separator with the lower plug fitted thereto in FIG. 7 to separate the solutions layer by layer using the centrifuge.
Figure 13:
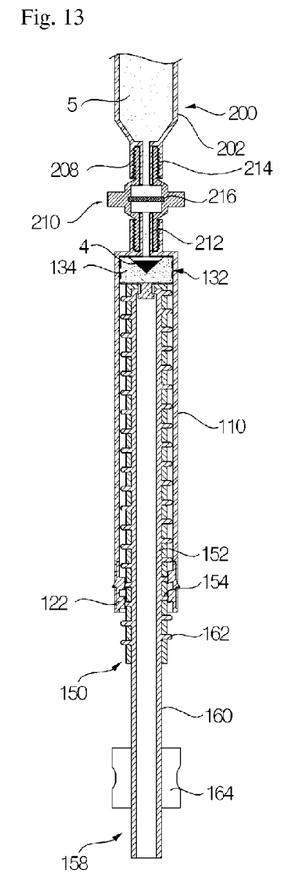
FIG. 13 is a cross-sectional view illustrating the state that the ingredient collector is connected to the ingredient separator with the upper plug removed therefrom through the connector in FIG. 12, and liquid components placed in the upper side of the ingredient separator are pushed up by pressing upward the pressing screw body to supply the components into the ingredient collector connected to the ingredient separator through the connector.

Next, the ingredient separator 100 is inserted in the centrifuge (not shown) to separate the solution layer by layer. FIG. 12 illustrates the state that the solution is divided into a stem cell solution 4 collected in a concave groove 140 and a supernatant solution 5 placed over the stem cell solution 4. Then, fluids placed in the upper side are discharged by the same method as the above mentioned method of separating the blood components. In some embodiments, as shown in FIG. 13, almost all fluids are discharged except both the stem cell solution 4 collected in the collection portion and a minute amount of supernatant solution 5.

Again, a washing solution is supplied into the ingredient separator 100 through the flow tube 116 thereof. At this time, the pressing protrusions 162 are hidden in the push tube 150 by rotating the elastic tube using the grip 164 so as to easily retreat the plunger 132.

The ingredient separator 100 with the washing solution introduced therein is again inserted in the centrifuge to separate the solutions layer by layer.

Further, as mentioned above, almost all fluids are discharged except both the stem cell solution 4 collected in the collection portion and the minute amount of supernatant solution 5, and the washing solution is again injected therein. Then the process of separating the solutions layer by layer is repeated three or four times.

Figure 14:
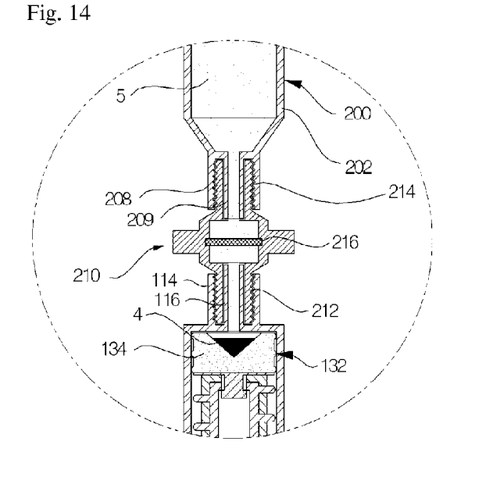
FIG. 14 is an enlarged cross-sectional view illustrating the connector for connecting the ingredient collector and the ingredient separator of FIG. 13.

Finally, the stem cell solution obtained from the collection portion is moved to a new ingredient collector 200. To extract the stem cell solution, as shown in FIG. 13, a connector 210 in which a cell strainer 216 is installed may be used. The connector 210 includes connector fitting portions 212 and 214 bilaterally. The connector fitting portions 212 and 214 may be screwed with both the tube fitting portion 114 and the connecting tube 208, respectively.

More specifically, after the stem cell solution is moved to the ingredient collector, the ingredient collector is connected to the one end of the connector with the cell strainer and a new ingredient collector is connected to the other end of the connector. Then, the process of meshing or cell straining the stem cell solution through the mesh of the cell strainer 216 is performed to complete the extraction thereof.

Generally, a portion of extracellular matrix may remain therein due to uncompleted dissolution even if the collagenase or enzyme treatment is performed. Therefore, if the meshing process of the stem cell solution is performed, it is possible to previously prevent the occlusion of a vessel occurring by the extracellular matrix during injecting the solution in a human body or thrombosis due to a mass of cells generated by entangling of cells. In this case, if a connector having two inlets formed in the top thereof is used, the processes of meshing the stem cell solution and adding a nutrient solution or drugs to the stem cell solution may be easily performed at the same time.

Figure 15:
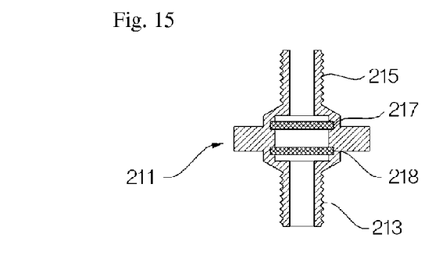
FIGS. 15 and 16 are cross-sectional views of other examples for the connector.

In particular, as shown in FIG. 15, if a connector 211 having a multi cell strainer structure which contains two or more cell strainers 217 and 218 is used, it is effective to separate fibrous tissues easily which are not digested by the collagenase enzyme. Herein, the cell strainer may have a different size of meshes (that is, the number of eyes per unit area of the cell strainer can be set differently). The connector 211 includes connector fitting portions 213 and 215 bilaterally thereof which are screwed with both the tube fitting portion 114 and the connecting tube 208, respectively.

Figure 16:
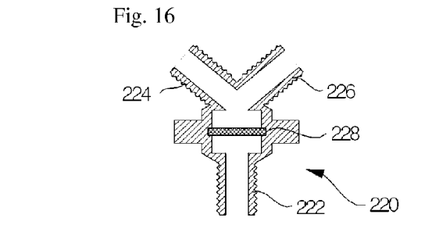

In addition, as shown in FIG. 16, if a connector 220 which includes one connector fitting portion 222 formed on one side thereof and two connector fitting portions 224 and 226 formed on the other side thereof is used, it is possible to simultaneously introduce drugs such as nutrient solutions to a stem cell solution. As a result the separation work can be performed easily and rapidly. Generally, it is easier to use the connector 220 having one cell strainer 228 in the view of forming molds.

Next, a method for separating bone marrow stem cells will be described. In the case of the bone marrow stem cells, bone marrows are firstly extracted from a site such as an iliac bone using a specific needle for extracting bone marrow, then the bone marrow stem cells may be extracted using the above mentioned method of separating the blood and the method of extracting adipose-derived stem cells.

Figure 17:
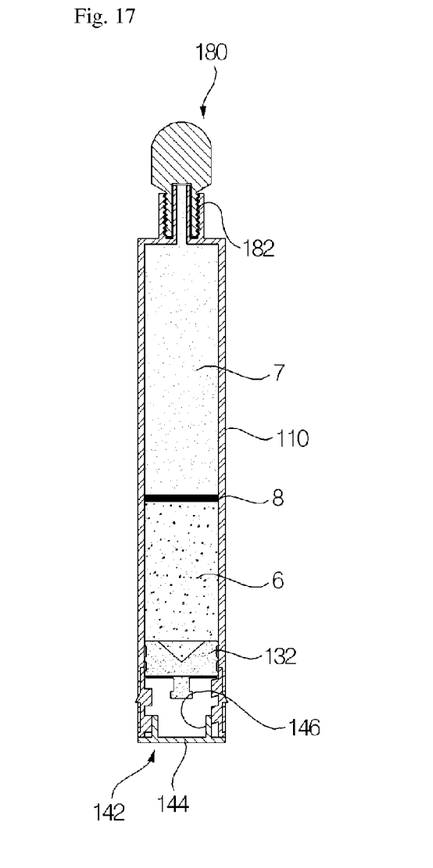
FIG. 17 is a cross-sectional view illustrating the state that bone marrow extracts are introduced in the ingredient separator with the lower plug fitted thereto in FIG. 7 to separate the extracts layer by layer using the centrifuge.

FIG. 17 is a cross sectional view illustrating the state that the layer separation is completed after centrifugation process in order to separate the bone marrow stem cells. The red blood cells 6, bone marrow stem cells 8, and plasma 7 are disposed from the lower side of the body in this order.

Further, if the above mentioned methods are used, it is possible to separate cells such as lymphocytes, immune cells, cord blood stem cells or the like using a gravity difference between the cells. That is, it is possible to separate either homologous cells or heterologous cells using the above mentioned method using the gravity difference between the cells.

Although embodiments of the present disclosure have been described in connection with the embodiments illustrated in the drawings, it is only illustrative. It will be understood by those skilled in the art that various modifications and equivalents can be made to the present disclosure. Therefore, the true technical scope of the present disclosure should not be defined by the appended claims.

The invention claimed is:

1. An ingredient separator comprising:
    a hollow body which includes a flow tube formed at one end portion thereof for communicating body fluids, and a stopper disposed at the other end portion thereof; and
    a plunger which is movably installed back and forth in the body to vary a space between the flow tube and a top thereof;
    wherein the plunger has a collection portion formed on the top thereof, and a backward movement of the plunger is limited by the stopper;
    wherein the stopper is a female screw unit which is coupled to the other end of the body,
    the body further includes a pressing unit which is inserted therein,
    wherein the pressing unit includes a pressing screw body to screw with the female screw unit, and a push tube having a plurality of tube holes formed on an outer periphery thereof,
    wherein the pressing screw body is an elastic tube, which is positioned in the push tube, and has a slit cutaway in a lengthwise direction thereof, and the pressing screw body has a plurality of pressing protrusions formed on the outer periphery thereof so as to be selectively inserted in holes of the push tube in a radial direction and screwed with a female thread formed in the female screw unit.

2. The ingredient separator according to claim 1, wherein the stopper has fixing protrusions which are detachably inserted in fixing holes formed in an end portion of the body.

3. The ingredient separator according to claim 1, wherein the stopper has a lower plug fitted therein to close an end of the body.

4. The ingredient separator according to claim 1, wherein the plunger has a coupling protrusion formed on a lower portion thereof facing the other end portion of the body through a neck portion, and the pressing screw body includes a latch portion fixed on one end portion thereof to engage with the neck portion when opposite faces defining the cutaway slit are in contact.

5. The ingredient separator according to claim 1, wherein a connector is fitted to the flow tube to connect an ingredient collector therewith.

6. The ingredient separator according to claim 5, wherein the connector has at least one cell strainer installed therein.

7. The ingredient separator according to claim 5, wherein the connector has one connector fitting portion formed on one side thereof and two connector fitting portions formed on the other side thereof, wherein each of the connector fitting portions are in fluid communication with each other.

8. The ingredient separator according to claim 6, wherein, when two or more cell strainers are installed inside the connector, each of the cell strainers has a different size of meshes with respect to each other.

* * * * *